United States Patent [19]
Hiramoto et al.

[11] Patent Number: 5,576,602
[45] Date of Patent: Nov. 19, 1996

[54] METHOD FOR EXTRACTING CHARGED PARTICLE BEAM AND SMALL-SIZED ACCELERATOR FOR CHARGED PARTICLE BEAM

[75] Inventors: Kazuo Hiramoto; Masahiro Tadokoro, both of Hitachiota; Junichi Hirota, Hitachi; Masatsugu Nishi, Katsuta; Akira Noda; Makoto Inoue, both of Kyoto, all of Japan

[73] Assignee: Hitachi, Ltd., Tokyo, Japan

[21] Appl. No.: 291,560

[22] Filed: Aug. 16, 1994

[30] Foreign Application Priority Data

Aug. 18, 1993 [JP] Japan ................... 5-204142

[51] Int. Cl.⁶ .................................. H05H 7/10
[52] U.S. Cl. ............................ 315/507; 315/501
[58] Field of Search .................. 315/500, 501, 315/503, 507

[56] References Cited

U.S. PATENT DOCUMENTS

| | | | |
|---|---|---|---|
| 3,896,392 | 7/1975 | Hudson et al. | 315/502 |
| 4,200,844 | 4/1980 | Nunan | 315/505 |
| 4,812,774 | 3/1989 | Tsumaki et al. | 315/501 |
| 4,996,496 | 2/1991 | Kitamura et al. | 315/501 |
| 5,101,169 | 3/1992 | Gomei | 315/503 |
| 5,117,194 | 5/1992 | Nakanishi et al. | 315/503 |
| 5,216,377 | 6/1993 | Nakata et al. | 315/501 |
| 5,285,166 | 2/1994 | Hiramoto et al. | 315/507 |
| 5,363,008 | 11/1994 | Hiramoto et al. | 313/62 |

OTHER PUBLICATIONS

AIP Conference Proceedings No. 127, 1983 pp. 52–61.

Primary Examiner—Alvin E. Oberley
Assistant Examiner—Lawrence O. Richardson
Attorney, Agent, or Firm—Antonelli, Terry, Stout & Kraus

[57] ABSTRACT

A circular accelerator is arranged to circulate a charged particle beam through a bending function provided by a bending magnet, set a tune of the charged particle beam being circulated as it is betatron-oscillated to a predetermined value through the effect of a quadrupole magnetic field, resonate the charged particle beam being circulated at the tune set to the predetermined value in a manner to increase an amplitude of the betatron oscillations over the stability limit of resonance, thereby extracting the charged particle beam. The circular accelerator includes a bending magnet formed to generate a quadrupole magnetic field component for horizontally focusing the charged particle beam being circulated and vertically defocusing the beam and another bending magnet formed to generate a quadrupole magnetic field component for horizontally defocusing the charged particle beam being circulated and vertically focusing the beam. The accelerator is reduced in size, easily operated, and enables to keep the location of the beam extraction and the diameter of the beam constant and output an excellent charged particle beam.

19 Claims, 10 Drawing Sheets

F I G. 12
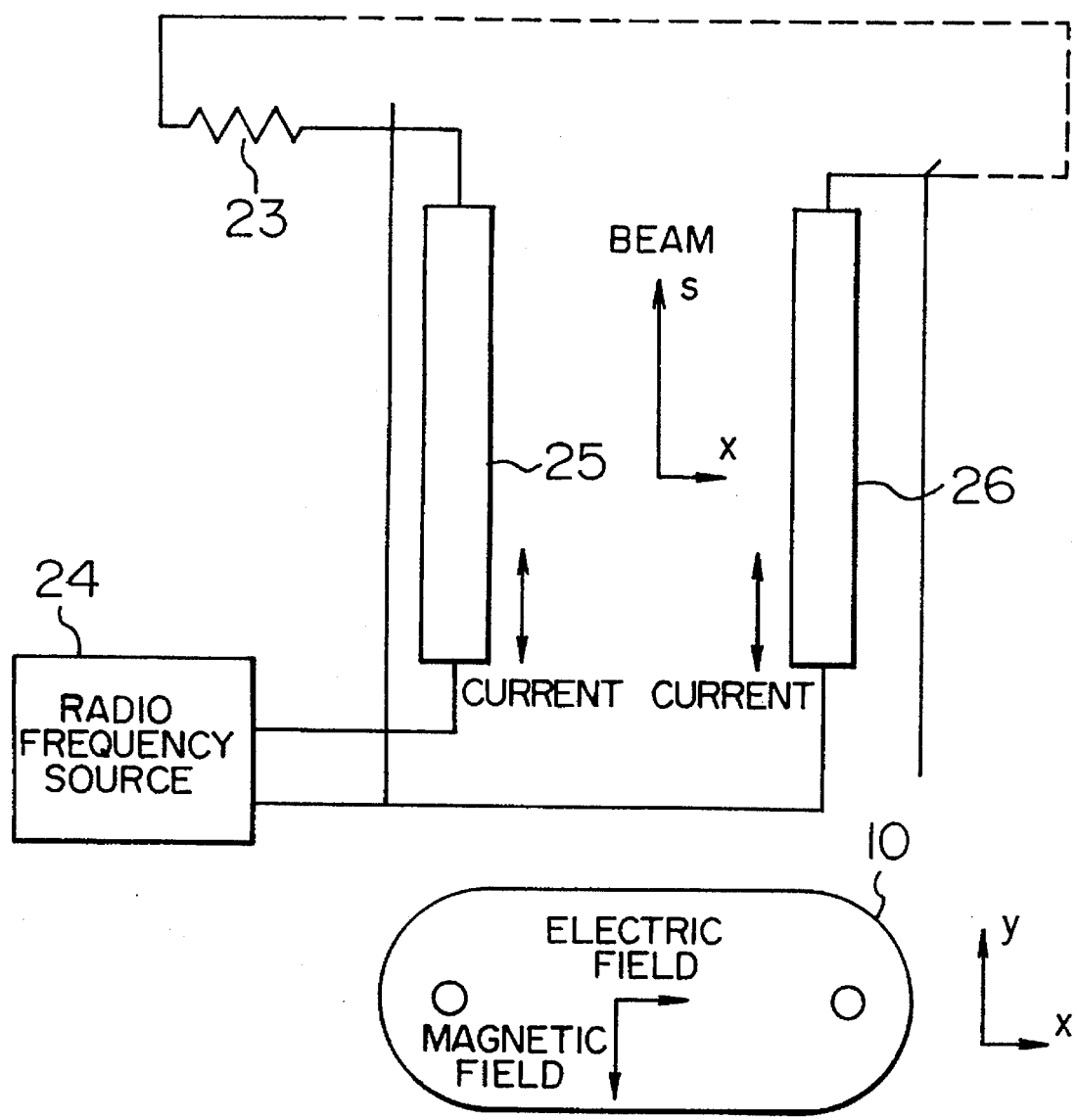

METHOD FOR EXTRACTING CHARGED PARTICLE BEAM AND SMALL-SIZED ACCELERATOR FOR CHARGED PARTICLE BEAM

BACKGROUND OF THE INVENTION

The present invention relates to an accelerator arranged to circulate a charged particle beam for boosting the beam energy and then to extract the beam and a medical apparatus to which the accelerator is applied. In particular, the invention relates to a small-sized accelerator which is preferable to easily obtaining the excellent charged particle beam with a constant beam diameter and a medical apparatus to which the small-sized accelerator is applied.

The conventional accelerator as shown in FIG. 1 is arranged to accelerate a charged particle beam and then to extract and transport the accelerated beam so that the beam may be used for a physical experiment or a medical purpose. The charged particle beam, which is injected from an accelerator 34 at the previous stage and then is introduced inside of a circular accelerator through the effect of an injector unit 15 and an injecting pulse electromagnet 35, is circulated along a beam central orbit 1 located at the center of a vacuum duct 10 as the beam is kept betatron-oscillated. Such a beam circulating type accelerator is ordinarily referred to as a circular accelerator. When the circular accelerator operates to extract the charged particle beam, the betatron oscillations occurring on the horizontal plane of the beam are resonated through the effect of a focusing quadrupole magnet 5, a defocusing quadrupole magnet 6 and a multipole magnet for exciting resonance 9 for increasing the amplitude of the betatron oscillations, so that the charged particle beam may be extracted from an extracting deflector 4, thereby utilizing the charged particle beam in a medical treatment room or a laboratory 33. Herein and hereafter, the term "magnet" refers to an electromagnet.

The focusing quadruple magnet 5 provides a horizontally focusing effect and a vertically defocusing effect. That is, if the magnet 5 is considered as an optical system, the focusing quadrupole magnet 5 horizontally corresponds to a convex lens or vertically corresponds to a concave lens. Likewise, the defocusing quadrupole magnet 6 provides a horizontally defocusing effect, that is, horizontally corresponds to a concave lens and a vertically focusing effect, that is, vertically corresponds to a convex lens. If the particles are resonated, the amplitude of the betatron oscillations of the particles is increased. To allow the particles to be extracted from the extracting deflector 4 without collision against the vacuum duct 10, there are provided extracting bump magnets 61 and 62 in the conventional accelerator.

The resonance of betatron oscillations is discussed in AIP Conference Proceedings, No. 127, 1983, pp. 52 to 61. This is a phenomenon to be discussed below. The charged particles are circulated as the particles are kept horizontally and vertically oscillated. This is called as betatron oscillations. The number of betatron oscillations per one circulation of a circular orbit is called as a tune. In a case that the tune is adjusted to come closer to an integer +⅓, an integer +⅔ or an integer +½ and at once a multipole magnetic field for exciting resonance is excited, among lots of charged particles being circulated, the charged particles having a larger amplitude of the betatron oscillations than a certain level abruptly increase their amplitude. This phenomenon is referred to as resonance of betatron oscillations. Further, the resonance given if the tune is adjusted to come closer to an integer +½ is referred to as second order resonance. The resonance given if the tune is adjusted to come closer to an integer +⅓ or an integer +⅔ is referred to as third order resonance. The border of resonance occurrence is referred to as stability limit of resonance. The magnitude of the stability limit changes depending on the strength of multipole magnetic field for exciting resonance and the value of a decimal part of the tune. The value of the tune is controlled by the intensity of the quadrupole magnetic field.

The later description will be expanded based on the case of the third resonance, that is, the case that the tune is adjusted to come closer to an integer +⅓. That is, assuming that the decimal part of the tune is $\Delta v$ (=0.33), in the multipole magnet for exciting resonance, the displacement of the betatron oscillations is substantially made equal at each of about $1/\Delta v$ circulation. If $\Delta v$ is equal to about 0.33, by applying such a magnetic field as effectively increasing the betatron oscillations to a beam of m-th circulation, (m+1)th circulation, or (m+2)th circulation, the beam displacement of m-th circulation is substantially same as that of (m+3)th circulation. Likewise, the beam displacement of (m+1)th circulation is substantially same as that of (m+4)th circulation and the beam displacement of (m+2)th is substantially same as that of (m+5)th. Hence, the amplitude of the betatron oscillations is remarkably increased. In particular, if $\Delta v$ comes closer and closer to ⅓, the same displacement of the betatron oscillations takes place at each of three circulations. The multipole magnetic field for exciting resonance is made more effective so that the amplitude of the betatron amplitude is likely to abruptly increase. That is, the stability limit of resonance is made smaller as the deviation of the tune from an integer +⅓ is made smaller and as the multipole magnetic field for exciting resonance is made stronger. As such, the conventional apparatus is arranged to take the steps of adjusting the tune to come closer to an integer +⅓, resonating the charged particles having a larger amplitude of betatron oscillations, selected among the charged particles being circulated, then making the tune come far closer to an integer +⅓ for reducing the stability limit of resonance, and thereby resonating the charged particles having a smaller amplitude of betatron oscillations. The tune control is executed by controlling the strength of the magnetic field of the quadrupole magnets 5 and 6 provided on the circular orbit shown in FIG. 1, that is, the current of the quadrupole magnets 5 and 6.

The particles in which the betatron oscillations are resonated are likely to increase their oscillation amplitudes and reduce a distance between the inner wall of the vacuum duct 10 and the particles as the particles are circulating more and more and more. The extracting bump magnets 61 and 62 are used for shifting the central orbit 1 of the oscillated beam locally toward the extracting deflector 4 before the extraction in order that the beam may be taken out of the extraction deflection 4 before the particles collide against the inner wall of the vacuum duct. The orbit locally moved by the bump magnets is referred to as a bump orbit. FIG. 2 shows a bump orbit 11 linearly indicated between the bump magnets 61 and 62. In FIG. 2, a numeral 20 denotes an electrode of the extracting deflector 4, in which the resonated particles, that is, the particles having an amplitude of increased oscillations, are extracted from the electrode 20 to the outside. In FIGS. 1 and 2, two bump magnets for extraction are provided. In place, four or five bump magnets may be used. The bump orbit 11 is moved in the extracting process in order to keep the orbit of the beam extracted by the extracting deflector 4 constant. Hence, plural bump magnets operate to change the strengths of their magnetic fields in the process of extraction, respectively.

On the other hand, as the prior art, there has been proposed a method for increasing the amplitude of the betatron oscillations and thereby bringing about resonance while keeping the tune constant, that is, each strength of the magnetic fields of the quadrupole magnets 5 and 6 constant. The apparatus arrangement for this prior art is shown in FIG. 3. This apparatus arrangement is different from that shown in FIG. 1 is provision of a unit for applying a radio frequency 14. As described in U.S. patent application Ser. No. 07/958, 161 Kazuo Hiramoto et al., filed Oct. 8, 1992, now U.S. Pat. No. 5,363,008, all disclosure thereof being incorporated herein by reference, the apparatus is arranged to control the tune to be constant, that is, the excitations of the quadrupole magnets 5 and 7 to be constant, or exciting the multipole magnet 9 for exciting resonance, and applying a radio frequency to a beam through the effect of the unit 14 for the purpose of increasing the amplitude of betatron oscillations and thereby causing the resonance. By this operation, this apparatus enables to extract a beam having a small diameter. When the beam is extracted, like the prior arts shown in FIGS. 1 and 2, the bump magnets are excited so as to form a bump orbit.

The foregoing prior art has the following problems.

As a first problem, the accelerator is made larger because lots of quadrupole magnets are required to be installed.

As a second problem, the control is made complicated, because lots of quadrupole magnets are required to be controlled.

As a third problem, the bump magnets are required to be provided for amending the change of an orbit of an extracted beam. This enlarges the accelerator more. Further, the associative control of the bump magnets is made complicated in the process of extracting a beam.

SUMMARY OF THE INVENTION

It is an object of the present invention to provide an accelerator which provides a simplified and small-sized arrangement and an easy controllable function and enables to obtain a charged particle beam and a medical apparatus to which the accelerator is applied.

The object is achieved by providing a circular accelerator arranged to circulate a charged particle beam through the bending effect of a bending magnet, set the tune of the charged particle beam being circulated as the beam is betatron-oscillated to a predetermined value through the effect of a quadrupole magnetic field, bring about resonance of the charged particle beam being circulated at the tune of the predetermined value, increase the amplitude of the betatron oscillations up to the stability limit, and extract the charged particle beam, the circular accelerator being composed of plural pairs of a first bending magnet having such a pole form as causing a quadrupole magnetic field component allowing the charged particle beam being circulated to be horizontally focused and the beam to be vertically defocused and a second bending magnet having such a pole form as causing a quadrupole magnetic field component allowing the charged particle beam being circulated to be horizontally defocused and the beam to be vertically focused.

The charged particle beam is circulated not along the central orbit of the vacuum duct of the accelerator but as it is betatron-oscillated horizontally and vertically around the central orbit. When the beam is extracted, the resonance of the betatron oscillations is used. Thus, the present invention is arranged to provide the bending magnet with a quadrupole magnetic field function in consideration of the tune. Hence, the invention does not need to provide the quadrupole magnets, so that it may be reduced in size and more easily controlled and output an excellent charged particle beam.

BRIEF DESCRIPTION OF THE DRAWINGS

FIG. 12 is a schematic block diagram showing a unit for applying a radio frequency included in the first embodiment;

DESCRIPTION OF THE PREFERRED EMBODIMENTS

Later, an embodiment of the present invention will be described with reference to the drawings.

Figure 4:
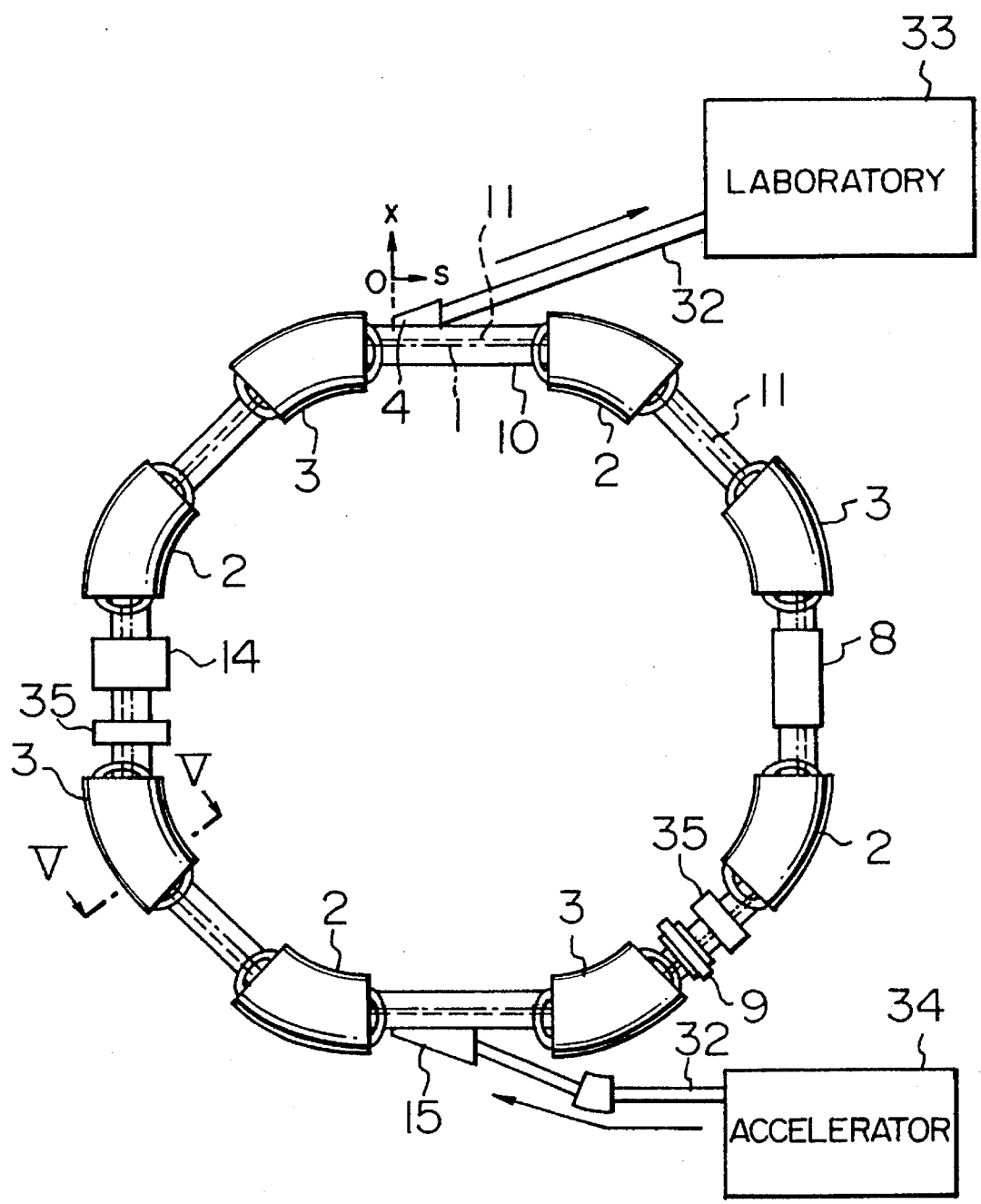
FIG. 4 is a schematic plane perspective showing an accelerator for a charged particle beam according to a first embodiment of the present invention.

FIG. 4 shows a circular accelerator according to the embodiment of the invention. This circular accelerator is arranged to have an injector unit 15 and an injecting pulse magnet 35 for injecting a charged particle beam extracted by an accelerator 34 located at the previous stage and passed through a beam transporting system, a radio frequency accelerating cavity body 8 for accelerating the charged particle beam being circulated in the circular accelerator, a bending magnet 2 provided with a focusing quadrupole magnet, a bending magnet 3 provided with a defocusing quadrupole magnet, a multipole magnet 9 for generating a stability limit of resonance, a radio frequency applying unit 14 for increasing the amplitude of the betatron oscillations of the charged particle beam until it exceeds the stability limit of resonance, and an extracting deflector. The circular accelerator of this embodiment does not use the bump magnets 61 and 62 for extraction and quadrupole magnets 5 and 6, which have been provided in the conventional circular accelerator.

The radio frequency applying unit 14 operates to increase the amplitude of the betatron oscillations of the beam over the stability limit of resonance so that the betatron oscillations may be resonated. When this resonance is generated, the conventional circular accelerator keeps the stability limit constant by controlling the power of lots of quadrupole magnets to be constant. This embodiment, however, keeps the stability limit constant through the effect of the bending magnets 2 and 3 without using any quadrupole magnet. Hence, the bending magnet of this embodiment is arranged to generate a dipole magnetic field for bending as well as a quadrupole (or more pole) magnetic field by selecting the form of the magnetic pole. The excitation of the coils of the bending magnets 2 and 3 makes it possible to generate a proper quadrupole magnetic field. That is, the forms of the magnetic poles of the bending magnets 2 and 3 are selected to keep a tune proper and the current passing through the bending magnets 2 and 3 is increased so that the beam reaches the target energy. If so, the tune required for extracting the beam is automatically achieved in the state of terminating the acceleration. In addition, to generate the resonance by the multipole magnet 9 provided for causing the resonance in this embodiment, the multipole magnetic field is required. The multipole magnetic field may be generated by the bending magnet.

As mentioned above, this embodiment is arranged so that the bending magnets 2 and 3 may generate a proper quadrupole magnetic field. Hence, this embodiment does not need a lots of quadrupole magnets whose control is very complicated, while the conventional circular accelerator uses them. This makes it possible to reduce the circular accelerator in size, reduce the peripheral length of the accelerator to be 20 m or less and simplify the driving operation.

Figure 2:
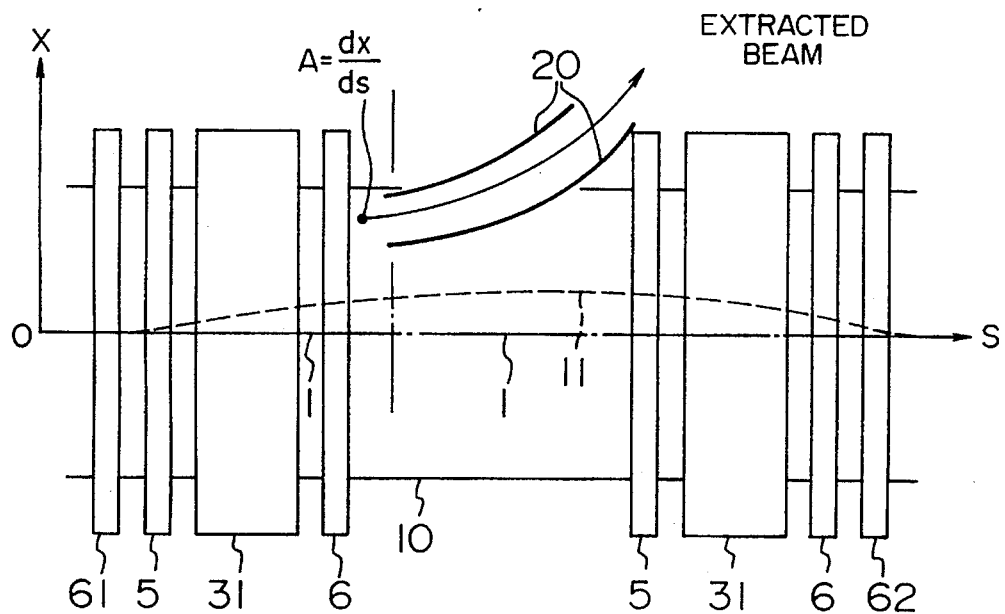
FIG. 2 is a schematic block diagram showing a bump orbit of the conventional accelerator.
Figure 3:
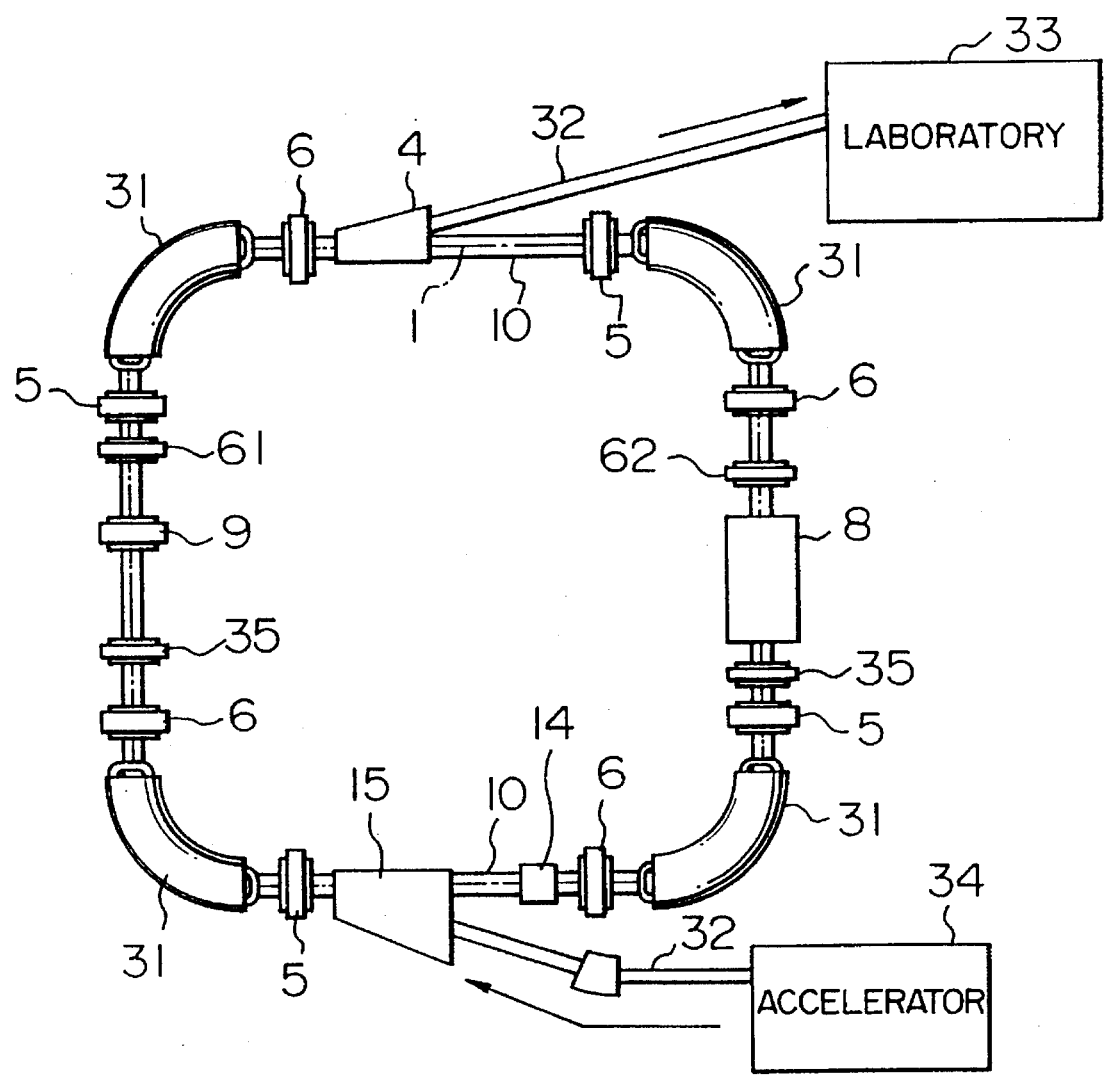
FIG. 3 is a schematic plane perspective showing another example of the conventional accelerator for a charged particle beam.

In the accelerator for accelerating the beam and extracting the accelerated beam, the maximum length of a linear part is defined by the lengths of the quadrupole magnets 5, 6 and the extracting deflector 4 as shown in FIG. 2. The conventional circular accelerator needs a length of 2 m or more. As described above, the circular accelerator according to the invention does not need any quadrupole magnet and thereby is arranged to suppress the linear part to be 2 m or less, thereby allowing the overall accelerator to be reduced in size. The peripheral length of the accelerator is also lessened by about 20 m or less. Further, the driving operation may be simplified.

Figure 5:
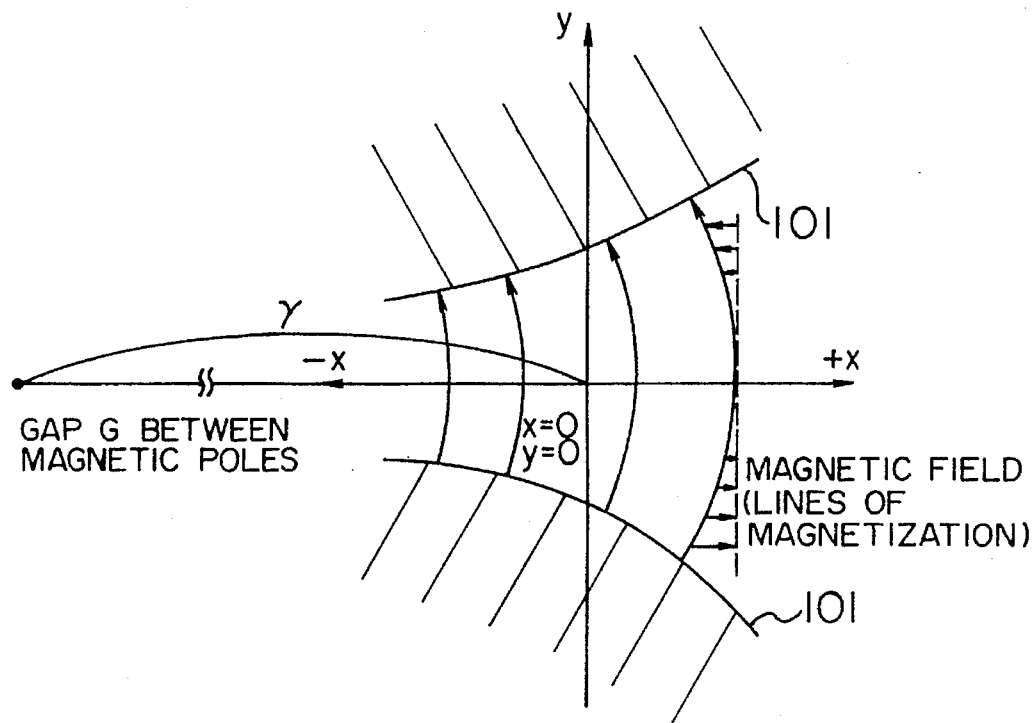
FIG. 5 is an explanatory view showing how a bending magnet in the first embodiment brings about a quadrupole magnetic field component.

FIG. 5 is a view showing a magnetic pole of the bending magnet 3 provided with the defocusing quadrupole magnetic function for generating a quadrupole magnetic field and a part of a gap between the magnetic poles and shows the section cut on V-V' of FIG. 4. In FIG. 5, the beam travels as if the beam is coming out of the drawing paper. A numeral 101 denotes a part facing to the gap between the magnetic poles. The center of the curvature of the magnet is located in the negative side of x so that the gap size may be progressively increased toward the positive side of x, that is, the radially outer side. That is, the gap width y at the spot separated by the distance r from the center of the curvature is adjusted to be $y = y_o (r/\rho)^n$ (n>1) with a constant of $y_o$, wherein $\rho$ is a curvature radius of the bending magnet and is a distance between the center of the curvature shown in FIG. 5 and x=y=0.

As a result, as will be understood from the direction of the magnetic field shown in FIG. 5, on the plane of y=0, the magnetic field is restricted only to the component of the y-axial direction. The relation between the location of the x-axial direction and the vertical magnetic field may be substantially represented by a linear function. That is, the quadrupole magnetic field is generated. The vertical magnetic field is reduced progressively and radially toward the outer side. The beam is shifted radially outwardly with respect the beam passing through the location of x=0 and has a larger curvature radius of an orbit. As such, the beam shifted radially outwardly is likely to be off the beam passing through the location of x=0. Further, the beam which is shifted radially inwardly with respect to the beam passing through the location of x=0 has a smaller curvature radius. As such, the beam shifted radially inwardly is likely to be off the beam passing through the location of x=0. These result in bringing about a horizontal defocusing function.

Next, consider the beam behavior in the case that the vertical distance is increased from the origin plane of y=0. In this case, the horizontal magnetic field is linearly increased, in which the direction of the horizontal magnetic field on the plus side of the y axis is opposite to that caused on the minus side of the y axis. In any case, however, the force of returning the beam to the plane of y=0 takes place. Hence, in the y direction, that is, vertically, the focusing function is provided to the beam. The magnitude of the focusing or the defocusing function may be controlled by changing a gap G, that is, properly selecting a value of n.

In the above description, the description has been expanded in the case that a value of n is equal to or more than 1. In the below description, the description has been expanded in the case that a value of n is equal to or less than 1.

At first, for n<0, the size of the vertical gap G is made smaller radially toward the outside of the beam. As a result, the vertical magnetic field is made stronger radially toward the outside of the beam, so that the horizontal focusing function may take place. On the other hand, the horizontal magnetic field is made stronger as the value on the y axis is increased or decreased from the origin plane of y=0, in which the directions of the horizontal magnetic fields are opposite to the above directions. In this case, the vertical defocusing function takes place. That is, the foregoing horizontal defocusing function is made to be a focusing function, while the foregoing vertical focusing is made to be a defocusing function. In the case of n=0, no vertical focusing or defocusing function is provided, while the focusing function is horizontally provided.

As mentioned above, for n<0, the vertical defocusing function is provided for n=0, no vertical focusing or defocusing function is provided, Hence, for 0<n<1, vertically, the focusing function is provided. However, horizontally, it means that when n enters into 0<n, the focusing function is maintained for a while before bringing about the defocusing function, because the horizontal focusing function takes place at n=0. As a result, for 0<n<1, the horizontal and vertical focusing functions take place.

As set forth above, it has been understood that the strength of the focusing function or the defocusing function is allowed to be controlled by changing the gap G, that is, properly selecting a value of n.

Figure 6:
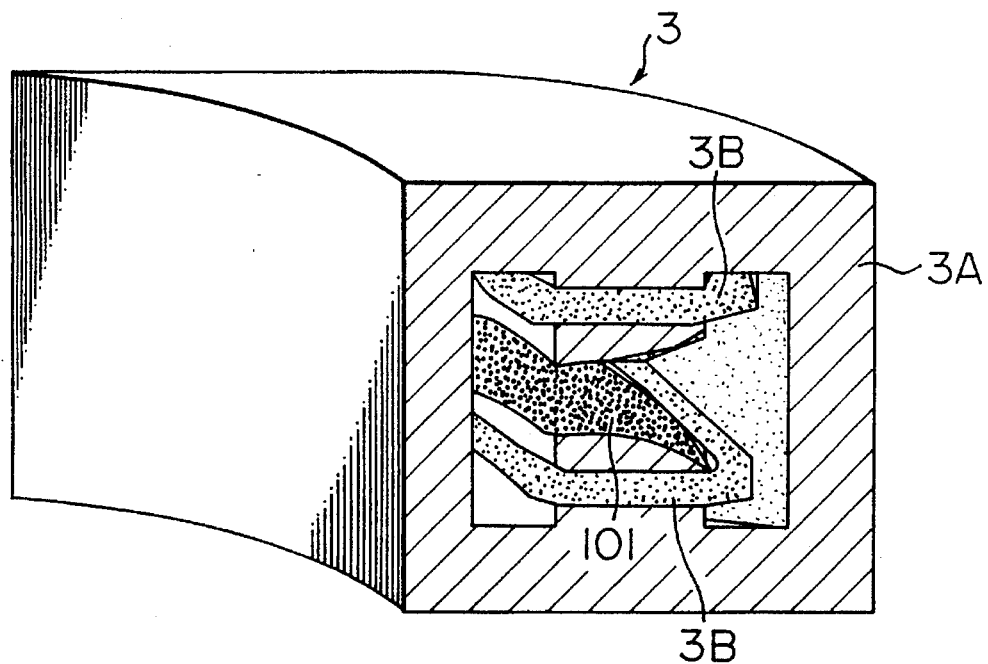
FIG. 6 is a perspective view showing how a bending magnet in the first embodiment brings about a quadrupole magnetic field component.

FIG. 6 is a section partially showing the bending magnet 3 provided with the defocusing quadrupole magnet, in which a pair of coils 3B are wound around the part 3A in order that a gap G may be formed between the magnetic poles.

The circular accelerator includes the bending magnet 2 arranged to make the value of n negative. The arrangement makes it possible to provide a quadrupole magnet function having a horizontal focusing effect in addition to such an original function as bending the orbit of the beam. The bending magnet 3 is arranged to make the value of n larger than 1. This arrangement makes it possible to provide a quadrupole magnet function having a horizontal defocusing effect and a vertical focusing effect in addition to such an original function as bending the orbit of the beam.

In turn, the description will be oriented to how the bump magnet used in the prior art is eliminated for further reduction in size in the present embodiment. As shown in FIG. 4, the coordinate system is configured so that the beam circulating direction is denoted by s and the horizontal direction is denoted by x. On the x axis, the center of a vacuum duct is set to 0 and the radial outside of the beam is set to a positive part of the axis. Later, how the beam is horizontally extracted will be described with respect to the third resonance, for example.

Figure 7:
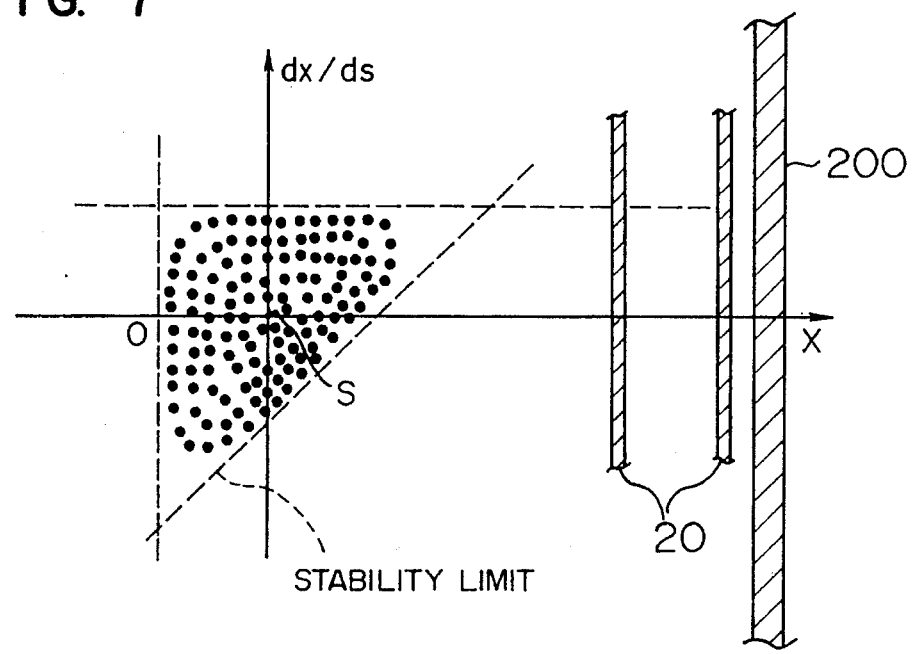
FIG. 7 is a view showing a phase space of the charged particle beam being circulated within the stability limit of resonance in the first embodiment.

On the condition that each of the bending magnets 2 and 3 is activated to generate the quadrupole magnetic field required to adjust the horizontal tune to come closer to an integer $\pm\frac{1}{3}$ and at once the magnet 9 is activated to generate the multipole magnetic field required for causing resonance, the stability limit of resonance is kept constant. FIG. 7 shows a relation (phase space) between x and dx/ds at each circulation of the beam in the case of S=S0, in which so denotes an s-directional installing location of the injector unit 4 shown in FIG. 4. Broken lines of FIG. 7 indicate the stability limit on the phase space. If the amplitude of the betatron oscillations is equal to or more than the stability limit, the resonance allows the oscillations amplitude to abruptly increase at each circulation of the beam. The increase of the oscillations amplitude leads to increase of charged particles to be rushed against the vacuum duct. Then, in order to allow the charged particles to be extracted from the extracting deflector 4 before the charged particles are rushed against the vacuum duct, the present embodiment is arranged so that over one circulation of the acceleration the central orbit of the beam is shifted from the orbit indicated by the numeral 1 of FIG. 4 to the side of the extracting deflector 4 by the bending magnet before extracting the beam. The shifted central orbit of the beam is denoted by a numeral 11 of FIG. 4.

Figure 8:
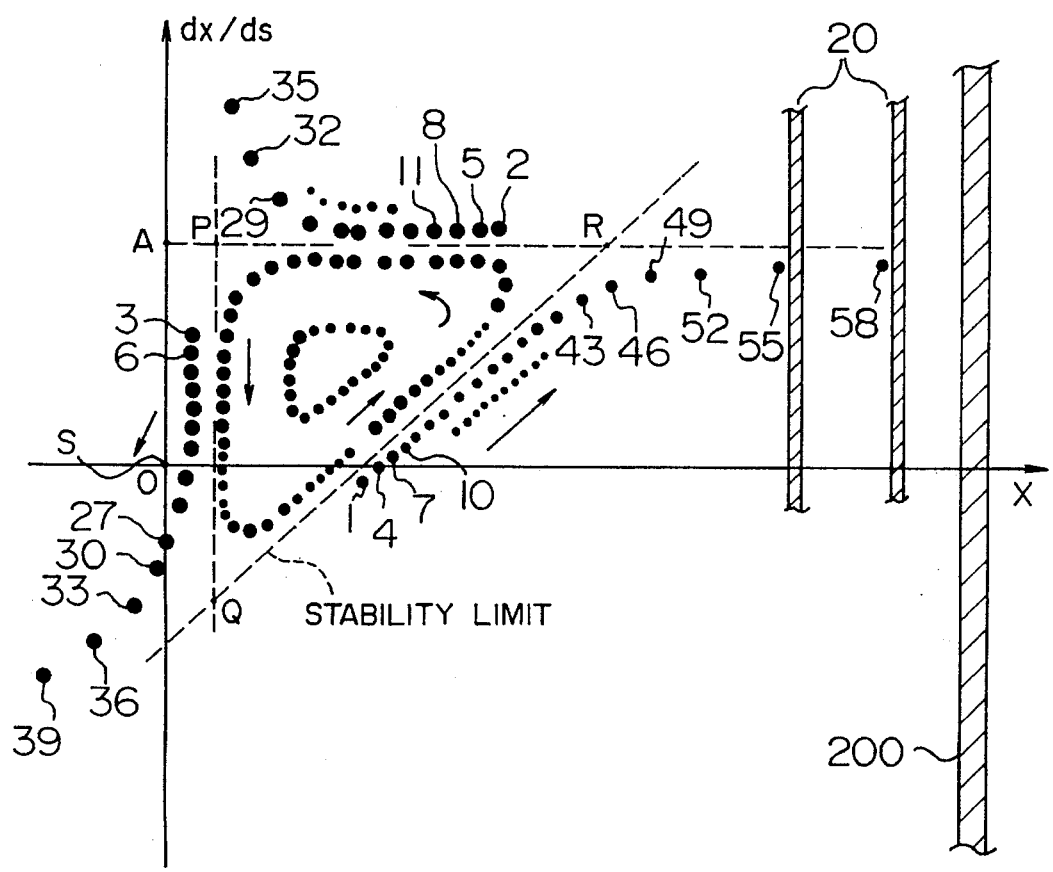
FIG. 8 is a view showing phase spaces of the resonated charged particle beam and of the charged particle beam being circulated within the stability limit of resonance like FIG. 7.

In this state, the phase space of S=S0 of FIG. 4 is shown in FIG. 8. In FIG. 8, a numeral 20 denotes two electrodes provided in the extracting deflector 4. A numeral 200 denotes a vacuum duct wall. Though not shown in FIG. 8, at the symmetric negative location on the x axis, likewise, the vacuum duct wall 200 is provided. With the shift of the central orbit of the beam, the center of the stability limit comes closer to the two electrodes 20 provided in the extracting deflector 4 as compared with the phase space at the S=S0 as shown in FIG. 7. After the central orbit of the beam is shifted, the radio frequency noises are applied to the beam. This results in increasing the amplitude of the betatron oscillations in a manner that the particles sequentially exceed the stability limit in the order of larger to smaller amplitudes of the betatron oscillations. The number of FIG. 8 indicates the number of circulations. As is understood from FIG. 8, the substantially same displacement appears at each three circulations. However, the particles having exceeded the stability limit gradually increase their oscillation amplitudes. Then, those particles are extracted from the electrode 20 of the extracting deflector 4 at an orbit gradient of dx/ds=A. By keeping the stability limit constant, the extracting orbit gradient is allowed to be constant. Hence, the circular accelerator of this embodiment does not need the bump magnet used in the prior art. Further, it does not also need to shift the central orbit of the beam by changing the magnetic field strength of the magnet in the extracting process, which has been necessarily executed in the prior art.

Figure 1:
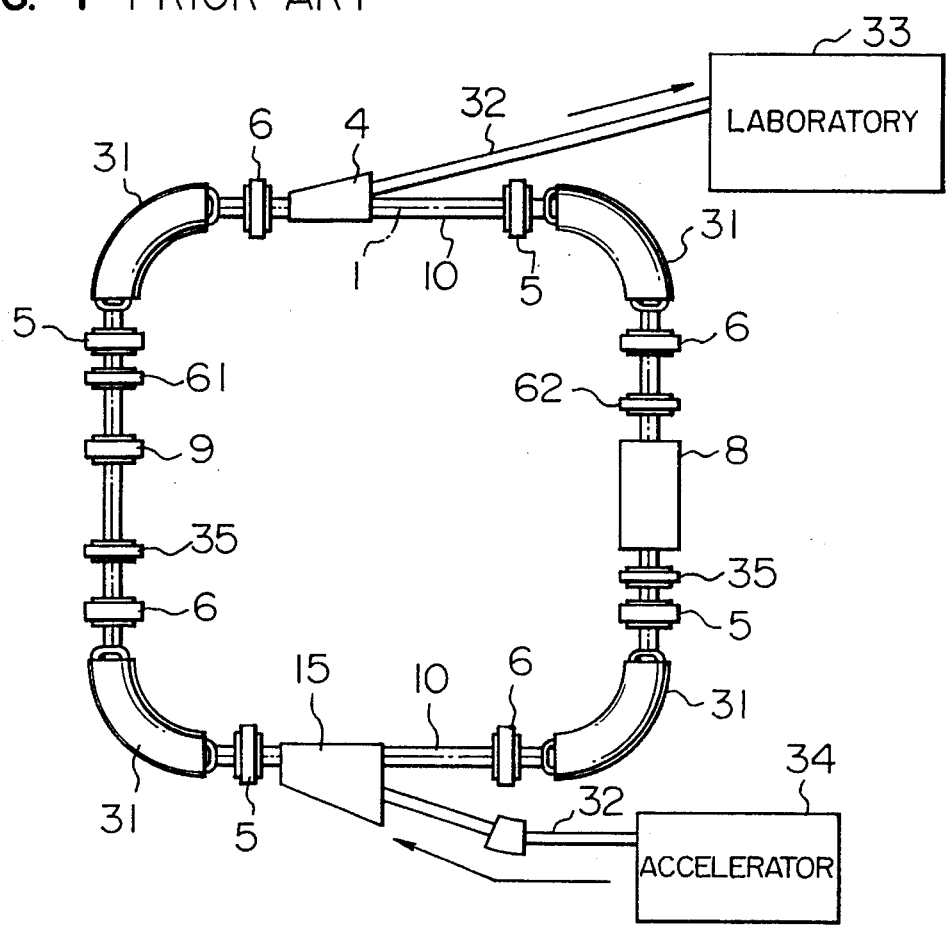
FIG. 1 is a schematic plane perspective showing the conventional accelerator for a charged particle beam.

As mentioned above, the circular accelerator of this embodiment enables to shift the central orbit of the beam on the average without having to use the bump magnet. This is because a lots of quadrupole magnets are removed and the quadrupole magnetic field is generated merely by the bending magnet. If the conventional accelerator shown in FIG. 1 changes only the power of the bending magnet, the central orbit of the beam is not allowed to be shifted to the side of the extracting deflector on the average. This is done by the influence of the change of the orbit gradient given by lots of quadrupole magnets. As a result, the particles to be rushed against the vacuum duct are increased before extracting the beam. The beam loss is rather increased accordingly. It means that the conventional circular accelerator is arranged so that the bump magnet has to be used when extracting the beam. The circular accelerator according to the present embodiment, however, is arranged to provide a function of generating a quadrupole magnetic field with the bending magnet for keeping the tune constant, that is, keeping the stability limit of resonance constant and apply a radio frequency to beam for increasing the amplitude of the betatron oscillations of the beam. This arrangement results in allowing the bump magnet to be removed.

To increase the amplitude of the betatron oscillations of a particle staying within the stability limit of resonance, there have been proposed the following methods of;

(1) applying an electric field or a magnetic field varying with time to the beam, and (2) rushing the other particles rather than the extracting beam against the beam being extracted.

In the case of using the magnetic field in the method (1), if the extracting plane is horizontal, the magnetic field is applied vertically (in the y-axial direction), while if the extracting plane is vertical, the magnetic field is applied horizontally (in the x-axial direction), for repetitively changing the orbit gradient of the beam. Though the regular or irregular time variation of the magnetic field may be acceptable, it is preferable that the frequency on which the magnetic field is changed with time comes closer to a frequency of the betatron oscillations, that is, a value given by multiplying the tune by a circulating frequency. In the case of using the electric field in the method (1), the electric field is required to be applied in the circulating direction, that is, the s direction of the beam, if the extracting plane is horizontal, in the horizontal direction (x-axial direction), if the extracting plane is vertical, in the vertical direction (y-axial direction). If the electric field is applied in the s direction of the beam, the beam energy changes, which brings about the change of a curvature radius of the orbit when the beam passes through the bending magnet. This change leads to the change of the central orbit of the betatron oscillations. This results in causing the change of the amplitude of the betatron oscillations. If the electric field is applied in the x-axial or the y-axial direction, like the magnetic field, the orbit gradient of the beam is changed for magnifying the amplitude of the betatron oscillations. The above change of the magnetic field with time holds true to the change of the electric field with time.

For the method of (2), which uses the effect of increasing the amplitude of the betatron oscillations as a result of the change of the orbit gradient done by the collision, this is executed on the same principle as the method of (1) using the electric field.

Hereafter, the embodiment of the invention will be more concretely described.

In the circular accelerator shown in FIG. 4, protons having energy of about 20 MeV are injected and are accelerated until the energy is boosted to 100 MeV. Then, the protons are extracted. A hexapole magnet 9, the radio frequency applying unit 14, and the extracting deflector 4 are used only in the process of extracting the accelerated beam whose energy is boosted to the target.

Figure 9:
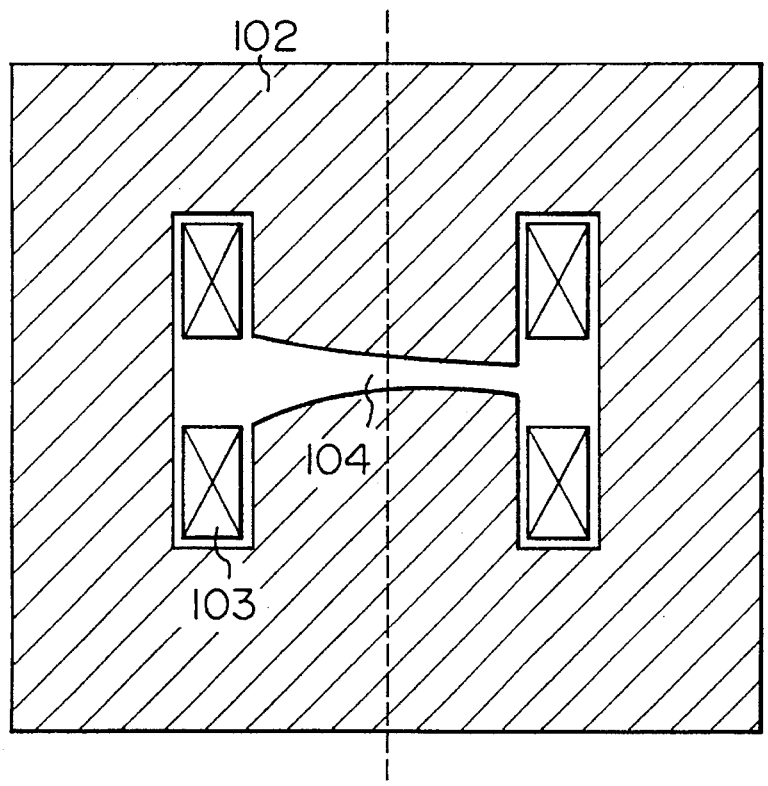
FIG. 9 is a schematic section showing the bending magnet shown in FIG. 4.
Figure 10:
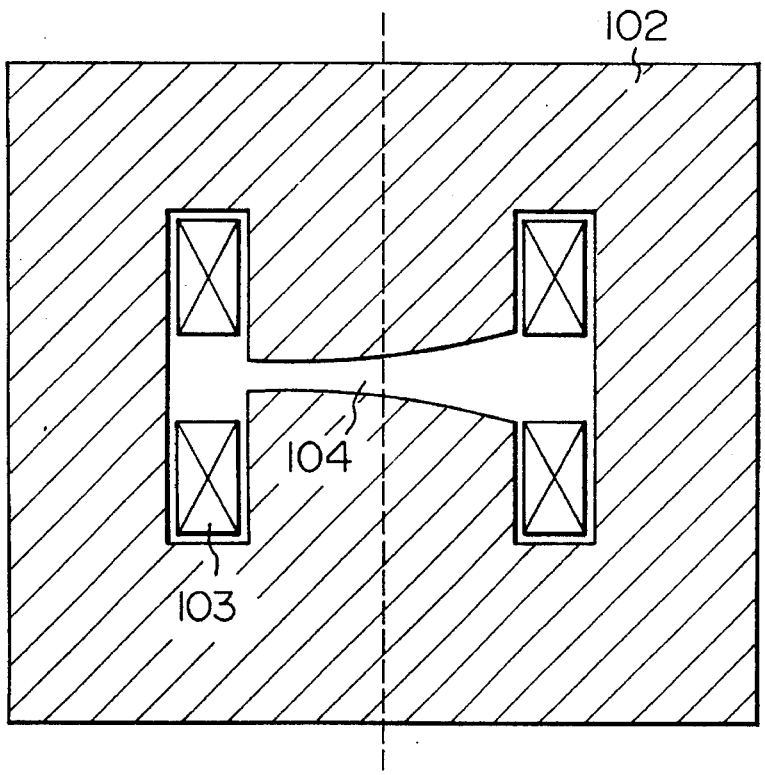
FIG. 10 is a schematic section showing the bending magnet shown in FIG. 4.

The orbit of the beam injected by the injector unit 15 is bent by the bending magnets 2 and 3 while the beam is circulated. At a time, the bending magnets 2 and 3 operate to change the orbit gradient by the force proportional to the shift from the central orbit 1 of the beam. The bending magnet 2 exerts to change the orbit gradient in a manner to horizontally focus the beam or vertically defocus the beam. That is, the bending magnet 2 has a negative n index and has a sectional structure as shown in FIG. 9. The bending magnet 3 exerts to change the orbit gradient in a manner to horizontally defocus the beam or vertically focus the beam. That is, the bending magnet 3 has a negative n index and has a sectional structure as shown in FIG. 10. These bending magnets operate to circulate the beam along the orbit 1 as the beam is betatron-oscillated. The number of the betatron oscillations is defined by the strengths of the quadrupole magnetic fields of the bending magnets 2 and 3, that is, the magnitude of the n index. In this embodiment, the n indexes, that is, the pole forms of the bending magnets 2 and 3 are adjusted to set the horizontal tune nx to 1.70 and the vertical tune ny to 0.75. In this state, the beam is stably circulated in the accelerator, when the radio frequency accelerating cavity body 8 operates to apply the radio frequency energy having the frequency on which the beam is circulated to the beam being circulated. As the energy is being applied to the beam by the radio frequency accelerating cavity body 8, the passing currents of the bending magnets 2 and 3 are increased. The increases of the currents of the bending magnets lead to increasing the dipole magnetic fields and the quadrupole magnetic fields as keeping these fields at a constant ratio. That is, the beam energy is allowed to be boosted as keeping the tune constant.

Figure 11:
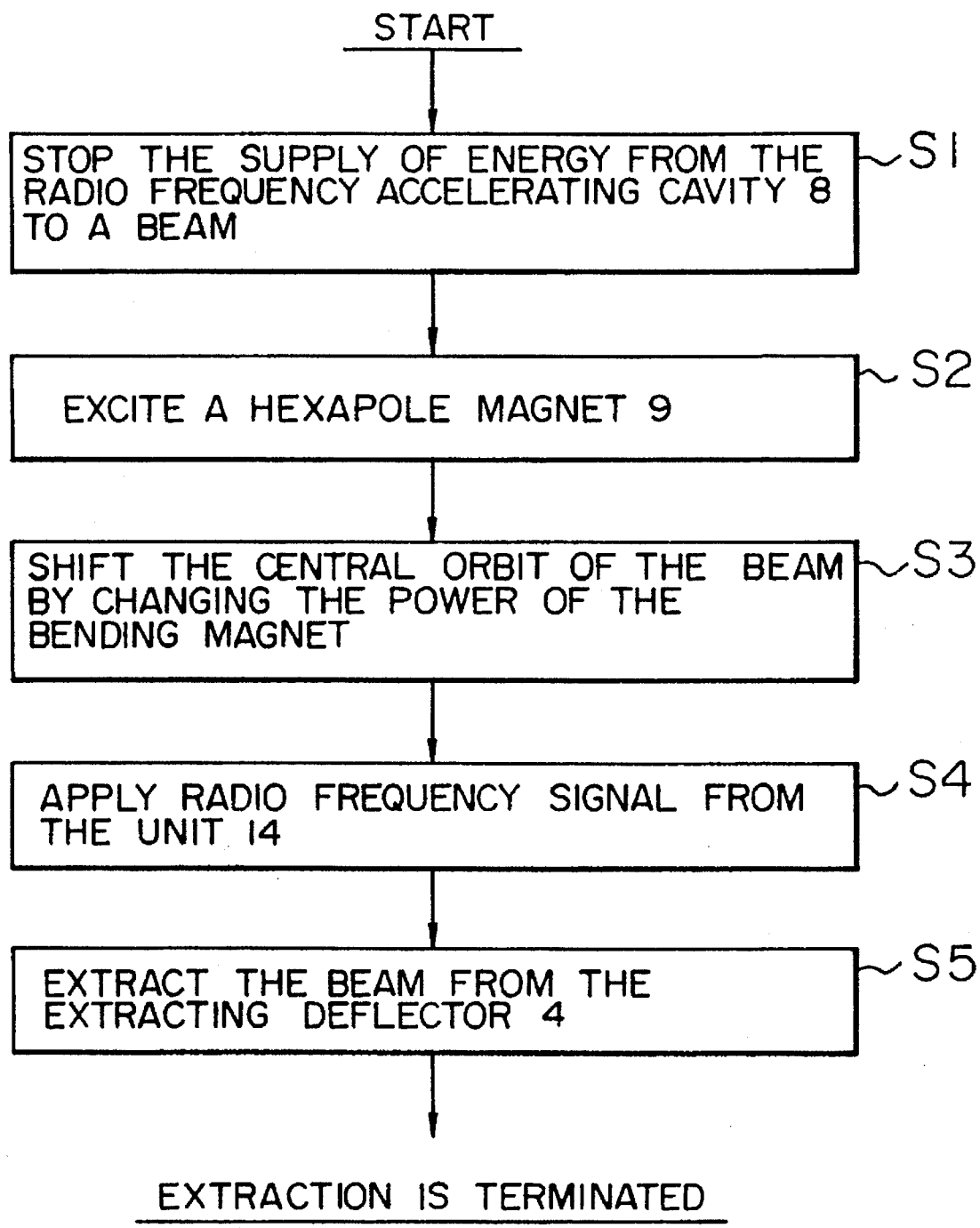
FIG. 11 is a flowchart showing a driving procedure to be executed when the charged particle beam is extracted in the first embodiment.

FIG. 11 is a flowchart showing an operating procedure for extracting the charged particles accelerated to hold the target energy. At first, at a step S1, the operation is executed to stop the supply of energy from the radio frequency accelerating cavity body 8 to a beam. Then, at a step S2, the current is fed to the hexapole magnet 9 for exciting resonance. At a step S3, the strength of the bending magnet is slightly diminished so as to shift the central orbit of the beam to the side of the extracting deflector over one circulation of the accelerator as shown by the broken line of FIG. 4. If the extracting deflector is located inside of the accelerator, conversely, the bending magnet is slightly made stronger so as to shift the central orbit of the beam to the inner side. FIG. 8 shows the trace in the phase space (x, dx/ds) at the extracting location s=so when the central orbit is shifted outwardly. A triangle PQR surrounded by the broken lines of FIG. 8 indicates the stability limit. The trace of the particles on the phase space is formed like a similar triangle whose size is different. The current to be flown to the hexapole magnet 9 is kept to be such a value that the particles of the beam being circulated are allowed to be held inside of the stability limit PQR if those particles have a large amplitude of betatron oscillations. The value is derived by calculation in advance or repeating the extracting operation.

At a next step S4, the operation is executed to enable the radio frequency applying unit 14 to apply an irregularly time-variable radio frequency, that is, radio frequency noises to the charged particle beam. FIG. 12 shows the structure of the radio frequency applying unit 14. In FIG. 12, numerals 25 and 26 denote bar-like electrodes, which are located horizontally in opposite to each other for enabling application of a time-variable signal. If the currents of opposite polarities are caused to flow through the bar-like electrodes, respectively, so that the magnetic field and the electric field oriented in the direction shown in FIG. 12 are applied to the charged particle beam. A numeral 23 denotes a load resistance, which connects both of the electrodes with each other so as to prevent the applied current from being reflected at the electrode end and returning to the power supply. By the effects of the magnetic field and the electric field, the orbit gradient of the beam changes so that the betatron oscillation amplitude of the beam within the phase space as shown in FIG. 8 begins to increase. The particles exceeding the stability limit are led between the two electrodes 20 of the extracting deflector 4 and then extracted out of the deflector 4, because the amplitude of the betatron oscillations of those particles are abruptly increased by resonance. Afterward, by applying the irregular signal to the electrodes 25 and 26, the amplitude of the betatron oscillations of the particles gradually increases. Even the particles having a small amplitude of the betatron oscillations at the initial stage exceed the stability limit as shown in FIG. 8 so that those particles are extracted through the extracting deflector 4 (step S5). In the phase space shown in FIG. 8, the stability limit is constant, so that the orbit gradient dx/ds of the extracted beam is also maintained as a constant A in the extracting process.

It is preferable that the radio frequency for increasing the betatron oscillations of the beam contains the frequency on which the betatron oscillations take place. The fundamental frequency of the betatron oscillations corresponds to a product of a circulating frequency and a decimal part of the tune. On the other hand, the beam being circulated contains the particles whose movements are shifted from the predetermined values given when the accelerator is designed. The tune of those particles is also shifted from the predetermined value. Further, when the multipole magnet is exerted, the tune of the particles having a large amplitude of the betatron oscillations is likely to shift from the tune of the particles having a small amplitude of the betatron oscillations. Hence, the radio frequency source 24 shown in FIG. 12 is arranged to feed a frequency spectrum having a width of about −0.05 fr with a frequency 0.7 fr as a center, in which fr denotes a circulating frequency. Moreover, the similar extraction can be realized if the similar width is held with (m+0.7)fr as a center.

As described above, by extracting the beam as keeping the stability limit constant, the extraction of the beam at a constant orbit gradient can be realized without having to use the extracting bump magnet and change the strength of the extracting deflector of the bending magnet in the extracting process. As such, the excellent charged particle beam whose diameter is small is allowed to be transported to a curing room (or experiment chamber) 33. If the change of the stability limit is about 20% or less, the change of the orbit gradient of the extracted beam is so light that no substantial difference between this change of the stability limit and the constant stability limit may take place. The magnitude of the stability limit is proportional to a difference between a decimal part (0.70 in this embodiment) of the tune and ⅔ or ⅓ (a difference between a decimal part of the tune and 0.5 in the case of the second resonance). Hence, by keeping the change of the tune 0.005 or less, it is possible to suppress the change of the stability limit to be 20% or less. That is, the similar extraction to the above can be executed.

Figure 13:
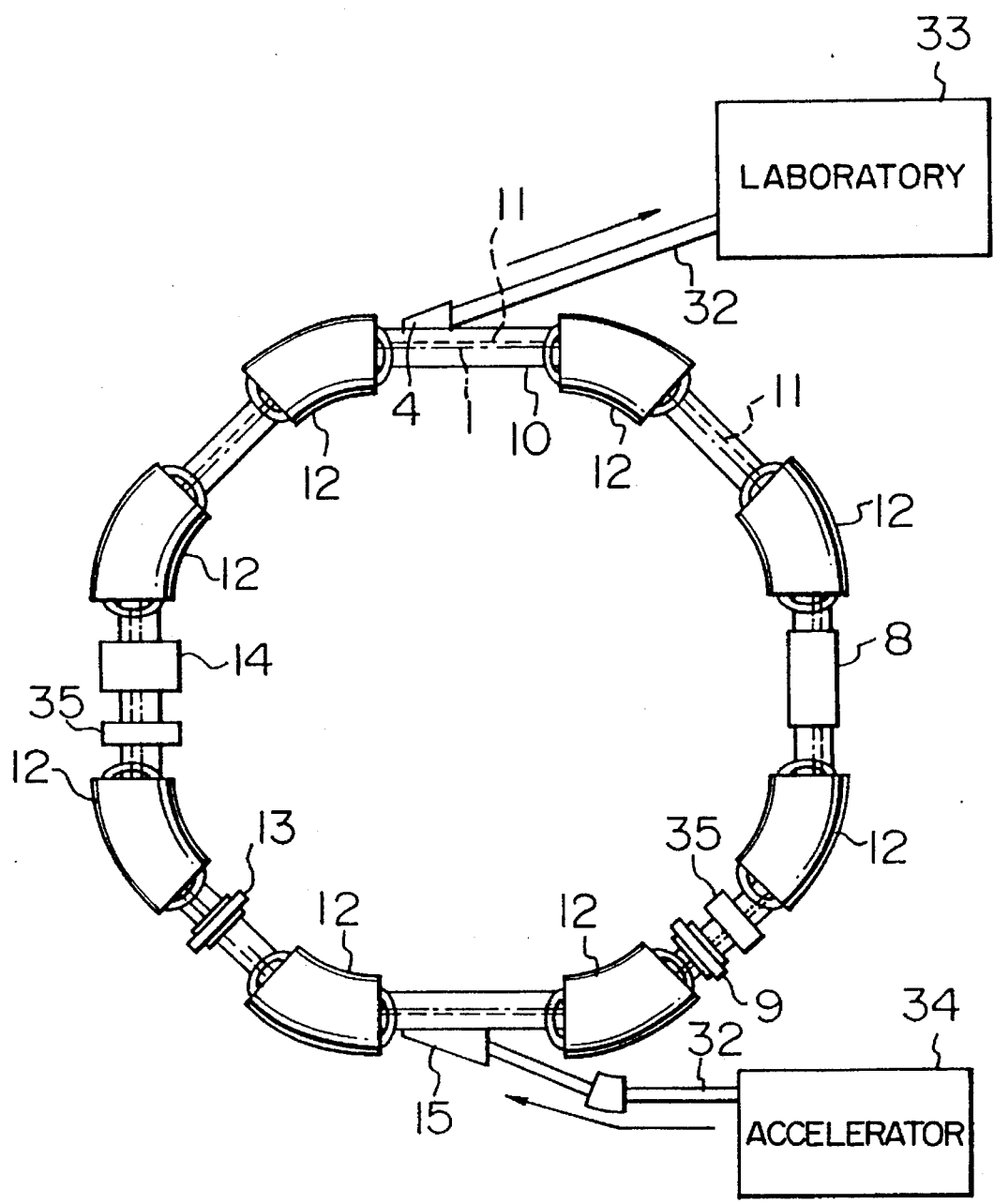
FIG. 13 is a schematic plane perspective showing an accelerator for a charged particle beam according to another embodiment of the present invention.

FIG. 13 is a view showing a circular accelerator according to a second embodiment of the present invention. The arrangement of the second embodiment is different from that of the first embodiment in the respect that just one kind of bending magnets are provided. The bending magnet 12 used in this embodiment is formed to spread the magnetic pole toward the radially outside. This bending magnet 12 has the n index described with respect to the first embodiment as a positive form. As described above, if the gap between the magnetic poles of the bending magnet is made gradually wider toward the radially outside, the bending magnet provides a vertically focusing effect on the beam. If the change of the gap is made so gradual as keeping n in the range from 0 to 1, the bending magnet provides a horizontally focusing effect on the beam. As such, the second embodiment is arranged to use one kind of bending magnets whose n index ranges from 0 to 1 and have the horizontal and the vertical focusing effects on the beam. The gap between the magnetic poles is adjusted so that the horizontal tune and the vertical tune are both set to be 0.75.

Figure 14:
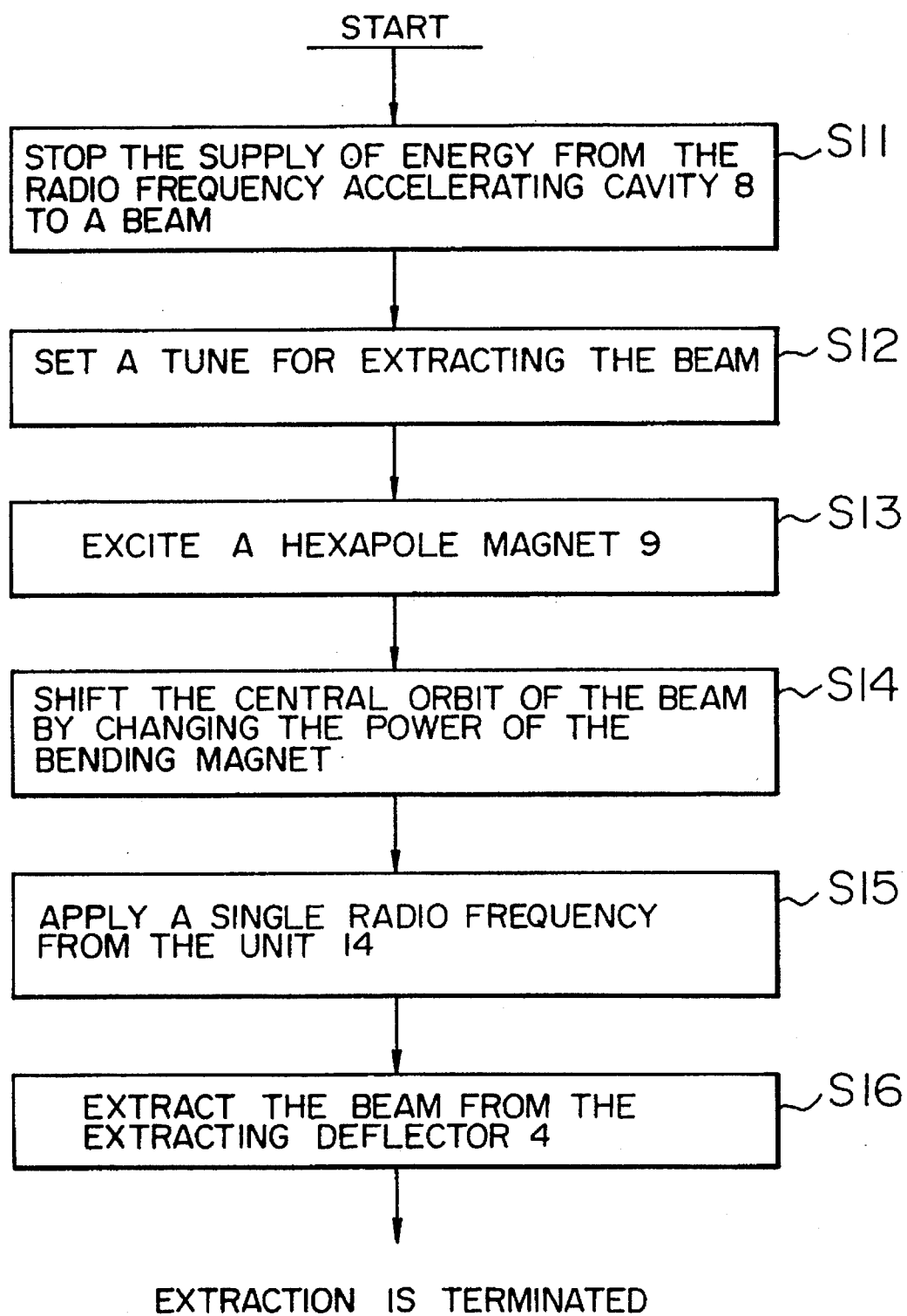
FIG. 14 is a flowchart showing a driving procedure to be executed when the charged particle beam is extracted in the first embodiment.

Further, the second embodiment provides one quadrupole magnet 13 by which the horizontal tune is changed from 0.75 to 0.70 before extracting the beam. In this embodiment, the changed tune is set as 0.70. In practice, it is just necessary to suppress a deviation of the decimal part of the tune from $\frac{1}{3}$, $\frac{2}{3}$ or $\frac{1}{2}$ to be 0.05 or less. After the beam is injected by the injector unit 15, by increasing the power of the bending magnet 12 as the radio frequency accelerating cavity 8 is applying radio frequency energy to the charged particle beam, the beam is accelerated so that the beam can reach the necessary energy. During this operation, the tune is kept constant. The flowchart showing the operating procedure given when the beam reaches the necessary energy is shown in FIG. 14.

After the beam obtains the necessary energy, as described at a step S11, the supply of the radio frequency energy is stopped. Then, as described at a step S12, the quadrupole magnet 13 is operated to set the horizontal tune to be 0.70. Then, the value is kept constant. At a step S13, the hexapole magnet 9 for exciting resonance is excited so that the stability limit of resonance is set to have a larger value than the amplitude of the betatron oscillations of the beam being circulated. At a next step S14, the power of the bending magnet 12 is made lower so that the central orbit of the beam is shifted to the side of the extracting deflector 4 for one circulation. After that, as keeping the power of the magnet constant, the radio frequency applying unit 14 is operated to apply a radio frequency for increasing the amplitude of the betatron oscillations to the beam (step S15). Then, at a step S16, the charged particle beam is extracted from the extracting deflector 4.

This embodiment is arranged to apply an a.c.signal having a frequency f from a power source for an a.c.signal having a single frequency to the beam. The frequency f is set to be equal to a product of a frequency on which the beam is circulated and a decimal part of a tune given when extracting the beam, that is, a value of 0.7. The application of the signal having such a frequency makes the period of an external signal applied from the electrode roughly coincide with the period of the betatron oscillations. This results in increasing the amplitude of the betatron oscillations of the particles staying within the stability limit of resonance to exceed the stability limit. Then, the beam is extracted like the first embodiment. As described with the first embodiment, however, the beam contains the particles whose tune is shifted from the predetermined value given when the accelerator is designed. Hence, the betatron oscillations of the beam does not sufficiently synchronize with the radio frequency applied to the beam, so that the accelerating speed of the betatron oscillation amplitude may be made lower. In this case, a radio frequency a.c. signal having a sufficient large amplitude, the beam is allowed to be extracted at high efficiency. In addition, the above description has concerned with the application of a radio frequency from the radio frequency applying unit 14. As mentioned above, the use of collision of the charged particle beam against the other particles makes it possible to increase the amplitude of the betatron oscillations. For example, by injecting inert gas when extracting the beam, the similar extraction can be realized.

The accelerator described with respect to the first or the second embodiment may apply to a medical device like that for cancer. In this case, the beam extracted from the extracting deflector 4 is transported to a curing room through a beam transporting system 32 for curing a patent. The use of the circular accelerator according to the embodiment makes it possible to extract the beam at a constant gradient. The resulting beam has a small beam diameter and hardly changes the location. Hence, the beam is suitable to the medical treatment. By controlling the strength of the radio frequency to be applied to the beam for increasing the amplitude of the betatron oscillations, it is possible to control the amount of the beam required for medical use. The strength of the radio frequency is controlled by predetermining a time-variable pattern, measuring a beam in the extracting process, and making the time-variable pattern closer to the optimum value as compared with a desired value, or feeding it back at the actual time.

The circular accelerator according to the present invention is small-sized and can be easily driven. Further, the accelerator provides a capability of extracting an excellent beam whose diameter and locational change is small.

What is claimed is:

1. An accelerator comprising:
   a radio frequency accelerating cavity body for accelerating a charged particle beam;
   a radio frequency applying unit for increasing an amplitude of betatron oscillations of said charged particle beam for making said beam exceed a stability limit;
   a multipole magnet for resonating the betatron oscillations of said charged particle beam having exceeded the stability limit;
   a first bending magnet for horizontally focusing said charged particle beam, vertically defocusing said beam and bending said beam; and
   a second bending magnet for horizontally defocusing said charged particle beam, vertically focusing said beam and bending said beam.

2. An accelerator as claimed in claim 1, wherein the change of said stability limit of resonance is suppressed to be 20% or less of the stability limit provided when the extraction is started.

3. An accelerator as claimed in claim 1, wherein the change of the tune occurring when said beam is extracted is suppressed to be 0.005 or less.

4. An accelerator as claimed in claim 1, wherein the amplitude of betatron oscillations is increased by a radio frequency having a single or multi-frequency component in a manner to excite resonance.

5. An accelerator as claimed in claim 1, wherein after the acceleration is terminated, the central orbit of the beam is shifted to the side of the extracting unit by means of a bending magnet before extracting said beam.

6. An accelerator as claimed in claim 5, wherein the change of the power of the bending magnet given when extracting the beam and is suppressed to be 1% or less.

7. An accelerator as claimed in claim 1, wherein the beam is controlled by changing the increasing speed of the amplitude of the betatron oscillations staying within the stability limit of resonance.

8. A medical apparatus comprising:

a curing room for doing medical treatment by a charged particle beam;

an accelerator as claimed in claim 1; and a transporting system for transporting said charged particle beam extracted by said accelerator to said curing room.

9. An accelerator according to claim 1, wherein the accelerator is arranged to circulate charged particles, and further comprising an extracting unit for extracting a charged particle beam, a linear part on which the extracting unit is installed having a length of 2 m or less.

10. An accelerator according to claim 1, wherein the accelerator is arranged to circulate charged particles and a peripheral length of the accelerator is 20 m or less.

11. An accelerator comprising:

a radio frequency accelerating cavity body for accelerating a charged particle beam;

a radio frequency applying unit for increasing an amplitude of betatron oscillations of said charged particle beam for making said beam exceed a stability limit;

a first bending magnet for resonating the betatron oscillations of said charged particle beam having exceeded the stability limit and bending said charged particle beam;

a second bending magnet for horizontally focusing said charged particle beam, vertically defocusing said beam and bending said beam; and a third bending magnet for horizontally defocusing said charged particle beam, vertically focusing said beam and bending said beam.

12. A medical apparatus comprising:

a curing room for doing medical treatment by a charged particle beam;

an accelerator as claimed in claim 11; and a transporting system for transporting said charged particle beam extracted by said accelerator to said curing room.

13. An accelerator comprising:

a radio frequency accelerating cavity body for accelerating a charged particle beam;

a radio frequency applying unit for increasing an amplitude of betatron oscillations of said charged particle beam for making said beam exceed a stability limit;

a multipole magnet for resonating a betatron signal of said charged particle beam having exceeded the stability limit;

a bending magnet for horizontally and vertically focusing said charged particle beam and bending said beam; and a quadrupole magnet for changing a horizontal tune of said charged particle beam.

14. An accelerator as claimed in claim 13, further comprising another bending magnet for generating a magnetic field component functioning to horizontally and vertically focusing the charged particle beam being circulated and adjusting the horizontal tune and a vertical tune to predetermined values; and a quadrupole magnet for slightly changing said predetermined value of the horizontal tune before extracting the beam.

15. An accelerator as claimed in claim 13, wherein said horizontal tune changed by said quadrupole magnet is made to have a deviation of 0.05 or less between its decimal part and any one of ⅓, ⅔ and ½.

16. A medical apparatus comprising:

a curing room for doing medical treatment by a charged particle beam;

an accelerator as claimed in claim 13; and a transporting system for transporting said charged particle beam extracted from said accelerator to said curing room.

17. An accelerator having plural magnets for circulating a charged particle beam and an extracting unit for resonating the betatron oscillations and extracting said charged particle beam through the effect of an extracting deflector, said magnets containing bending magnets for generating a dipole magnetic field component and a quadrupole or more-pole magnetic field component, the quadrupole magnetic field component of said bending magnet and the multipolar magnetic field of said bending magnet operating to causing a stability limit of resonance in concert and to increase an amplitude of said betatron oscillations for making said beam exceed the stability limit of resonance for exciting resonance, thereby extracting said beam.

18. An accelerator as claimed in claim 17, further comprising means for controlling a power of said bending magnets and means for applying a radio frequency signal to said beam for resonating said charged particle beam.

19. An accelerator having magnets for circulating a charged particle beam and an extracting unit for resonating betatron oscillations and extracting said charged particle beam from an extracting deflector, said magnets having bending magnets for generating a dipole magnetic field component and a quadrupole or more-pole magnetic field component, the quadrupole magnetic field generated by said quadrupole magnet and the multipolar magnetic field generated by said bending magnet operating to generate a stability limit of resonance in concert, increase an amplitude of said betatron oscillations for making said beam exceed the stability limit of resonance for exciting resonance, by extracting said beam.

* * * * *